(12) United States Patent
Lichtenstein

(10) Patent No.: US 9,526,866 B2
(45) Date of Patent: *Dec. 27, 2016

(54) CATHETER ENTANGLEMENT INDICATION

(71) Applicant: BIOSENSE WEBSTER (ISRAEL) LTD., Yokneam (IL)

(72) Inventor: Yoav Lichtenstein, Hod Hasharon (IL)

(73) Assignee: Biosense Webster (Israel) Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,654

(22) Filed: Mar. 14, 2016

(65) Prior Publication Data

US 2016/0193446 A1  Jul. 7, 2016

Related U.S. Application Data

(62) Division of application No. 12/851,085, filed on Aug. 5, 2010, now Pat. No. 9,307,927.

(51) Int. Cl.
*A61M 25/01* (2006.01)
*A61B 5/06* (2006.01)

(52) U.S. Cl.
CPC .......... *A61M 25/0127* (2013.01); *A61B 5/062* (2013.01); *A61M 2205/33* (2013.01)

(58) Field of Classification Search
CPC  A61B 5/062; A61M 2205/33; A61M 25/0127
See application file for complete search history.

(56) References Cited

U.S. PATENT DOCUMENTS

| | | |
|---|---|---|
| 5,060,632 A | 10/1991 | Hibino et al. |
| 5,352,197 A | 10/1994 | Hammersmark et al. |
| 5,368,015 A | 11/1994 | Wilk et al. |
| 5,391,199 A | 2/1995 | Ben-Haim |
| 5,921,978 A | 7/1999 | Thompson et al. |
| 6,056,699 A | 5/2000 | Sohn et al. |
| 6,239,724 B1 | 5/2001 | Doron et al. |

(Continued)

FOREIGN PATENT DOCUMENTS

| | | |
|---|---|---|
| JP | 11092847 A | 4/1999 |
| JP | 2000-10467 A | 1/2000 |

(Continued)

OTHER PUBLICATIONS

European Search Report mailed Dec. 12, 2011 in corresponding European Patent Application No. 11176625.9.

(Continued)

*Primary Examiner* — Ruth S Smith

(57) ABSTRACT

The present invention includes an apparatus having an elongated probe with proximal and distal ends and a sensor coupled to the elongated probe and configured to generate signals used for determining location and orientation coordinates of the elongated probe. The apparatus further includes a processor operatively connected to the sensor, and being configured to measure a cumulative angle of rotation that is applied by an operator to the proximal end of the probe while the operator manipulates the proximal end so as to move the distal end within a body of a patient. The apparatus also includes an output device operatively connected to the processor, and configured to present an indication of the cumulative angle of rotation to the operator.

9 Claims, 2 Drawing Sheets

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,585,650 B1 | 7/2003 | Solem |
| 6,618,612 B1 | 9/2003 | Acker et al. |
| 6,689,089 B1 | 2/2004 | Tiedtke et al. |
| 6,690,963 B2 | 2/2004 | Ben-Haim et al. |
| 7,585,273 B2 | 9/2009 | Adler et al. |
| 7,751,867 B2 | 7/2010 | Viswanathan |
| 8,007,506 B2 | 8/2011 | To et al. |
| 9,307,927 B2 * | 4/2016 | Lichtenstein .......... A61B 5/062 |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0114088 A1 | 6/2006 | Shachar |
| 2006/0278248 A1 | 12/2006 | Viswanathan |
| 2007/0123750 A1 | 5/2007 | Baumgartner et al. |
| 2010/0125253 A1 | 5/2010 | Olson et al. |
| 2010/0125276 A1 | 5/2010 | Palermo |
| 2011/0098571 A1 | 4/2011 | Medlin et al. |

FOREIGN PATENT DOCUMENTS

| | | |
|---|---|---|
| WO | WO 96/05768 A1 | 2/1996 |
| WO | WO 97/29803 A1 | 8/1997 |
| WO | WO 02/062265 A2 | 8/2002 |
| WO | WO 2006/116597 A2 | 11/2006 |

OTHER PUBLICATIONS

Examiner's Decision of Refusal mailed Sep. 8, 2015 in corresponding Japanese Patent Application No. 2011-170853.

* cited by examiner

CATHETER ENTANGLEMENT INDICATION

CROSS REFERENCE TO RELATED APPLICATIONS

This application is a divisional application of U.S. patent application Ser. No. 12/851,085, filed Aug. 5, 2010, now U.S. Pat. No. 9,307,927, the entire contents of which are hereby incorporated by reference.

FIELD OF THE INVENTION

The present invention relates generally to medical probes, and particularly to methods and systems for sensing and indicating probe rotation.

BACKGROUND OF THE INVENTION

When a physician manipulates a catheter during a medical procedure, the catheter may become twisted or tangled. Several methods and systems have been proposed in order to detect or avoid such situations. For example, U.S. Pat. No. 5,921,978, whose disclosure is incorporated herein by reference, describes a catheter that includes fluoroscopic marker components disposed in the catheter distal end, in order to provide enhanced fluoroscopic visibility. Some of the disclosed catheter configurations are used for providing visual information to the physician regarding the direction and degree of twist of the catheter distal end.

U.S. Pat. No. 5,352,197, whose disclosure is incorporated herein by reference, describes a turn limiter for a catheter with a twistable tip. The catheter has a flexible wall for use in complex twisting anatomy, and contains a torque wire or a torquable guide wire lumen. The torque wire or torquable guide wire lumen extends through the length of the catheter and is attached to the catheter at or near the distal end thereof. The proximal end of the torque wire protrudes from the proximal end of the catheter and is attached to a turn limiter. The turn limiter allows limited rotation of the proximal end of the torque wire or torquable guide wire lumen without axial dislocation.

SUMMARY OF THE INVENTION

An embodiment of the present invention that is described herein provides a method, including:

while an operator of an elongated probe, having proximal and distal ends, manipulates the proximal end so as to move the distal end within a body of a patient, automatically measuring a cumulative angle of rotation that is applied by the operator to the proximal end; and presenting an indication of the cumulative angle of rotation to the operator.

In some embodiments, measuring the cumulative angle of rotation includes sensing the cumulative angle of rotation using a sensor that is coupled to the probe. In an embodiment, the sensor includes a magnetic position sensor, and measuring the cumulative angle of rotation includes sensing one or more externally-applied magnetic fields using the magnetic position sensor and estimating the cumulative angle of rotation responsively to the sensed magnetic fields. In a disclosed embodiment, the sensor includes an acceleration sensor, and measuring the cumulative angle of rotation includes sensing an angular acceleration with respect to a longitudinal axis of the probe using the acceleration sensor and estimating the cumulative angle of rotation responsively to the sensed angular acceleration.

In some embodiments, the sensor is coupled to the proximal end of the probe. In alternative embodiments, the sensor is coupled to the distal end of the probe. In an embodiment, presenting the indication includes alerting the operator when the cumulative angle of rotation exceeds a predefined threshold. Additionally or alternatively, presenting the indication includes indicating to the operator a preferred rotation direction that would reduce the cumulative angle of rotation. Further additionally or alternatively, presenting the indication includes displaying the cumulative angle of rotation alphanumerically to the operator.

There is additionally provided, in accordance with an embodiment of the present invention, apparatus, including:

a processor, which is connected to an elongated probe having proximal and distal ends, and which is configured to measure a cumulative angle of rotation that is applied by an operator to the proximal end of the probe while the operator manipulates the proximal end so as to move the distal end within a body of a patient; and an output device, which is configured to present an indication of the cumulative angle of rotation to the operator.

There is also provided, in accordance with an embodiment of the present invention, a computer software product operating in conjunction with an elongated probe having proximal and distal ends, the product including a computer-readable medium, in which program instructions are stored, which instructions, when read by a computer, cause the computer to measure a cumulative angle of rotation that is applied by an operator to the proximal end of the probe while the operator manipulates the proximal end so as to move the distal end within a body of a patient, and to present an indication of the cumulative angle of rotation to the operator.

There is further provided, in accordance with an embodiment of the present invention, apparatus, including:

a probe, including:
an elongated body having distal and proximal end; and
a sensor, which is coupled to the body and is configured to generate signals that are indicative of a rotation applied to the proximal end by an operator; and
a processor, which is configured to estimate a cumulative angle of rotation responsively to the signals, and to present an indication of the cumulative angle of rotation to the operator.

The present invention will be more fully understood from the following detailed description of the embodiments thereof, taken together with the drawings in which:

DETAILED DESCRIPTION OF EMBODIMENTS

Overview

In some medical procedures, a physician navigates the distal end of a catheter in a patient's body. The physician moves the distal end by manipulating the proximal end of the catheter, e.g., using a handle fitted at the proximal end. In particular, the physician sometimes rotates the catheter about the catheter's longitudinal axis, for example in order to adjust the viewing angle or bending direction of the catheter tip, or to navigate along certain paths.

In most cases, either clockwise or counterclockwise rotation could be used to achieve the same result. In practice, however, a given physician tends to repeatedly rotate the catheter in the same direction (clockwise or counterclockwise). Excessive rotation in the same direction may cause the catheter body and/or interconnection cables to twist and entangle. This sort of twisting and entanglement may cause difficulty in maneuvering the catheter, and in some cases damage the catheter. In some cases the catheter cable has to be disconnected in order to untwist it.

Embodiments of the present invention that are described hereinbelow provide methods and systems for preventing excessive catheter rotation. The disclosed techniques automatically measure the cumulative rotation angle applied to the catheter's proximal end, and present an indication of the cumulative rotation angle to the physician. In an example embodiment, the cumulative rotation angle is measured using a magnetic position sensor that is fitted in the distal end of the catheter. In an alternative embodiment, the cumulative rotation angle is measured using a magnetic position sensor or an acceleration sensor that is fitted in the proximal end of the catheter, e.g., in the catheter handle.

Various indications can be presented to the physician based on the measured cumulative rotation angle. In one embodiment, the numerical value of the rotation angle is displayed to the physician on a monitor screen. In another embodiment, the physician is alerted when the cumulative rotation angle exceeds a maximum allowed value. In some embodiments, the physician is given an indication as to the preferred direction for subsequent rotation of the catheter (the direction that would reduce the cumulative rotation angle).

When using the disclosed techniques, catheter twisting and entanglement are reduced. As a result, catheter damage is avoided, and the physician can maneuver the catheter without interference. Although the embodiments described herein refer mainly to cardiac catheters, the disclosed techniques can be used with various other types of medical probes, such as endoscopes.

System Description

Figure 1:
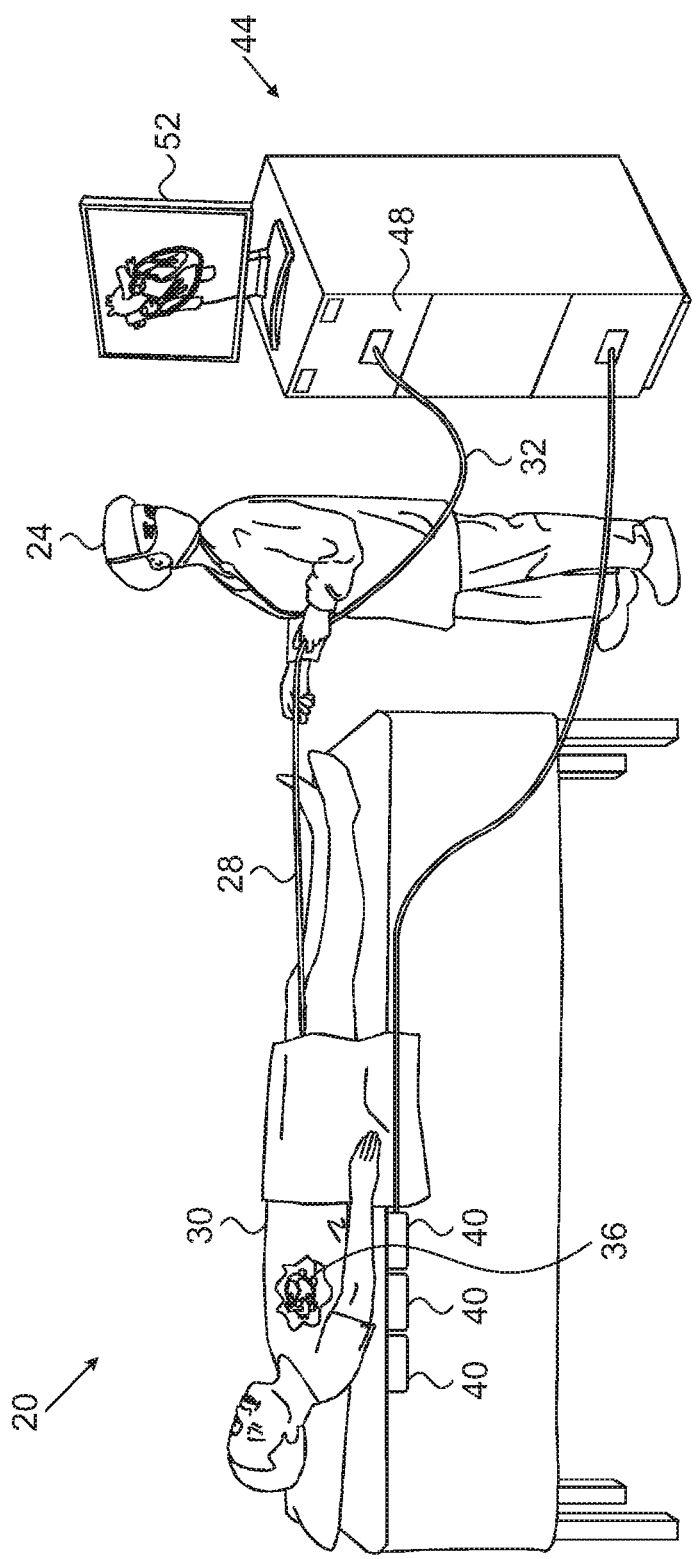
FIGS. 1 and 2 are schematic, pictorial illustrations of a system for magnetic position tracking that uses a cardiac catheter, in accordance with an embodiment of the present invention.

FIG. 1 is a schematic, pictorial illustration of a system 20 for magnetic position tracking that uses a cardiac catheter, in accordance with an embodiment of the present invention. System 20 may be based, for example, on the CARTO™ system, produced by Biosense-Webster Inc. (Diamond Bar, Calif.). In system 20, a physician 24 (or other operator) inserts a catheter 28 (or other probe) into the body of a patient 30. Catheter 28 has a proximal end that is handled by the physician, and a distal end 36 that is navigated through the patient body. Catheter 28 is connected to a control console 44 using a cable 32. In the embodiment described herein, catheter 28 is inserted into the patient's heart and used in creating electrophysiological maps of one or more heart chambers. Alternatively, catheter 28 may be used, mutatis mutandis, for other therapeutic and/or diagnostic purposes in the heart or in other body organs.

Console 44 uses magnetic position sensing to determine position coordinates of distal end 36 inside the heart. To determine the position coordinates, a driver circuit in console 44 drives field generators 40 to generate magnetic fields within the body of patient 30. Typically, field generators 40 comprise coils, which are placed at known positions below the patient's torso. A magnetic position sensor within distal end 36 of catheter 28 (shown in detail in FIG. 2 below) generates electrical signals in response to these magnetic fields. A processor 48 in console 44 processes these signals in order to determine the position coordinates of distal end 36, typically including both location and orientation coordinates. Magnetic position tracking methods of this sort are described in detail in U.S. Pat. Nos. 5,391,199, 6,690,963, 6,484,118, 6,239,724, 6,618,612 and 6,332,089, in PCT International Publication WO 96/05768, and in U.S. Patent Application Publications 2002/0065455, 2003/0120150 and 2004/0068178, whose disclosures are all incorporated herein by reference.

Based on the signals received from catheter 28, processor 44 drives a display 52 to present physician 24 with a map of cardiac electrophysiological activity, as well as providing visual feedback regarding the position of distal end 36 in the patient's body and status information and guidance regarding the procedure that is in progress.

Processor 48 typically comprises a general-purpose computer, with suitable front end and interface circuits for receiving signals from catheter 28 and controlling the other components of console 44. Processor 48 may be programmed in software to carry out the functions that are described herein. The software may be downloaded to processor 48 in electronic form, over a network, for example, or it may be provided on non-transitory tangible media, such as optical, magnetic or electronic memory media. Alternatively, some or all of the functions of processor 48 may be carried out by dedicated or programmable digital hardware components.

Detection and Prevention of Catheter Twisting and Entanglement

When conducting the medical procedure, physician 24 sometimes rotates catheter 28 about its longitudinal axis, for example in order to adjust the viewing angle or bending direction of the catheter tip, or to navigate along certain paths in the heart or vascular system. In most cases, either clockwise or counterclockwise rotation can be applied to achieve the same result. In practice, however, the physician tends to repeatedly rotate the catheter in the same direction (clockwise or counterclockwise), e.g., because of habit or convenience.

Excessive rotation of catheter 28 in the same direction may cause catheter 28 and/or cable 32 to twist and entangle. This sort of twisting and entanglement may cause difficulty in maneuvering the catheter, and in some cases damage the catheter or cable. In some embodiments of the present invention, system 20 comprises means for detecting over-rotation of catheter 28 in a certain direction, and for notifying physician 24 of the detected over-rotation.

In some embodiments, processor 48 measures the cumulative rotation angle that is applied to the catheter by the physician, and presents an indication of the measured cumulative rotation angle to the physician. Using this indication, the physician can be alerted when the catheter is over-rotated, and can perform subsequent rotations in the opposite direction. The term "cumulative rotation angle" refers to the total net rotation applied in a given (e.g., clockwise) direction about the catheter's longitudinal axis. For example, two complete clockwise turns are regarded as a cumulative rotation angle of +720°. Two complete counterclockwise turns are regarded as a cumulative rotation angle of −720°. Applying a complete clockwise turn followed by a 45° counterclockwise rotation produces a cumulative rotation angle of +315°. The choice of representing clockwise rotations using positive angles and counterclockwise rotations using negative angles is arbitrary, and the opposite convention can also be used.

Figure 2:
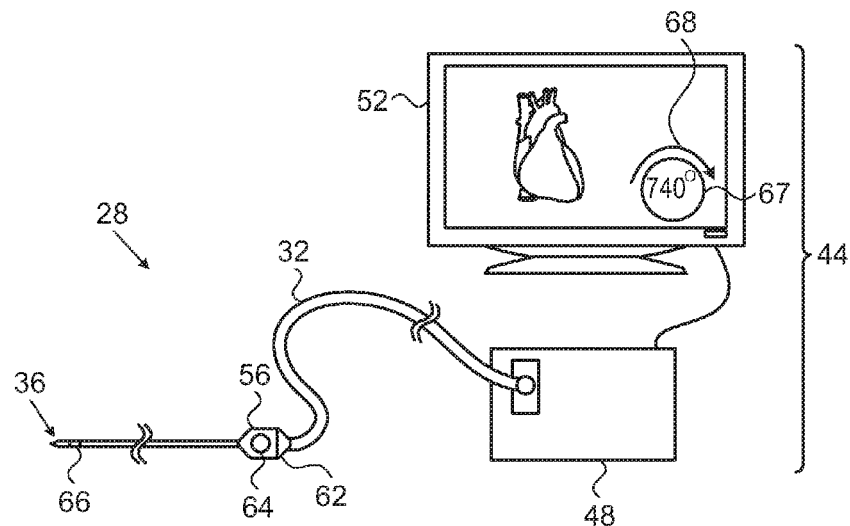

FIG. 2 is a schematic, pictorial illustration of certain elements of system 20, in accordance with an embodiment of the present invention. FIG. 2 shows catheter 28 and some of console 44 in greater detail. In the present embodiment, a handle 56 is fitted at the proximal end of catheter 28. The handle is used for maneuvering the catheter by the physician, and in particular for rotating the catheter about its axis. A connector 62 connects catheter 28 to cable 32. A magnetic position sensor 66 is fitted in distal end 36 of catheter 28, in order to carry out magnetic position tracking of the distal end by system 20, as explained above. In some embodiments, a sensor 64, e.g., a magnetic position sensor or an acceleration sensor, is coupled to the proximal end of the catheter, for example fitted in handle 56 or connector 62.

In some embodiments, processor 48 measures the cumulative rotation angle that the physician applies to catheter 28. In an example embodiment, processor 48 measures the cumulative rotation angle based on the signals produced by magnetic position sensor 66 in the distal end. In a typical application of this sort, system 20 measures the location and orientation coordinates of distal end 36 using the magnetic position tracking methods described above. In particular, processor 48 tracks the orientation of the distal end based on the signals produced by sensor 66, and calculates the cumulative rotation angle of the catheter.

In an alternative embodiment, processor 48 receives signals from sensor 64 in the proximal end of the catheter, and estimates the cumulative rotation angle based on these signals. In an example embodiment, sensor 64 comprises an acceleration sensor. In this embodiment, the signals are indicative of the angular acceleration of the catheter (in the present example of handle 56) about its longitudinal axis. Processor 48 processes these signals so as to estimate the cumulative rotation angle applied to the catheter. In an example embodiment, the processor integrates the measured angular acceleration to estimate the angular velocity of the catheter, and integrates the angular velocity to estimate the cumulative angle or rotation. In an alternative embodiment, sensor 64 comprises a magnetic position sensor, e.g., a sensor similar to sensor 66. In this embodiment, system 20 measures and tracks the position of sensor 64 similarly to the tracking of sensor 66. Using the signals produced by sensor 64, processor 48 estimates the cumulative rotation angle applied to the catheter.

In alternative embodiments, processor 48 may calculate the cumulative rotation angle based on inputs from two or more sensors, e.g., based on both sensor 66 at the distal end and sensor 64 at the proximal end. Further alternatively, processor 48 may measure or estimate the cumulative rotation angle applied to catheter 28 based on any other suitable sensor and using any other suitable method. Note that the disclosed techniques are in no way limited to use in magnetic position tracking systems such as system 20. For example, the methods described herein can be used with an acceleration sensor at the proximal end, without a position tracking system of any kind.

Typically, the signals produced by the sensor or sensors in the catheter produce signals that are indicative of the absolute rotation angle of the catheter, and not of the cumulative rotation angle. Computation of the cumulative rotation angle based on these signals is performed by processor 48.

In some embodiments, processor 48 presents an indication of the measured cumulative rotation angle to physician 24. In the example embodiment of FIG. 2, processor 48 displays an alphanumeric field 67 showing the present value of the cumulative rotation angle on display 52. Alternatively, processor 48 may display the present value of the cumulative rotation angle using any other suitable alphanumeric or graphical method.

In some embodiments, processor 48 alerts the physician when the cumulative rotation angle exceeds a predefined (positive or negative) threshold. This sort of alert enables the physician to start rotating the catheter in the opposite direction or otherwise avoid over-rotation of the catheter. Processor 48 may alert the physician using any suitable method, e.g., by displaying a certain message or icon on display 52 or by sounding an audible alert.

In some embodiments, processor 48 notifies the physician of a preferable rotation direction for future rotations. In other words, the processor notifies the physician of the rotation direction that would reduce the cumulative rotation angle. Thus, if the present cumulative rotation angle is positive (clockwise), processor 48 may recommend to the physician to perform subsequent rotations in a counterclockwise manner, and vice versa. In the example of FIG. 2, processor 48 displays an arrow 68, which indicates the recommended rotation direction to the physician. Alternatively, any other suitable indication method can also be used.

Figure 3:
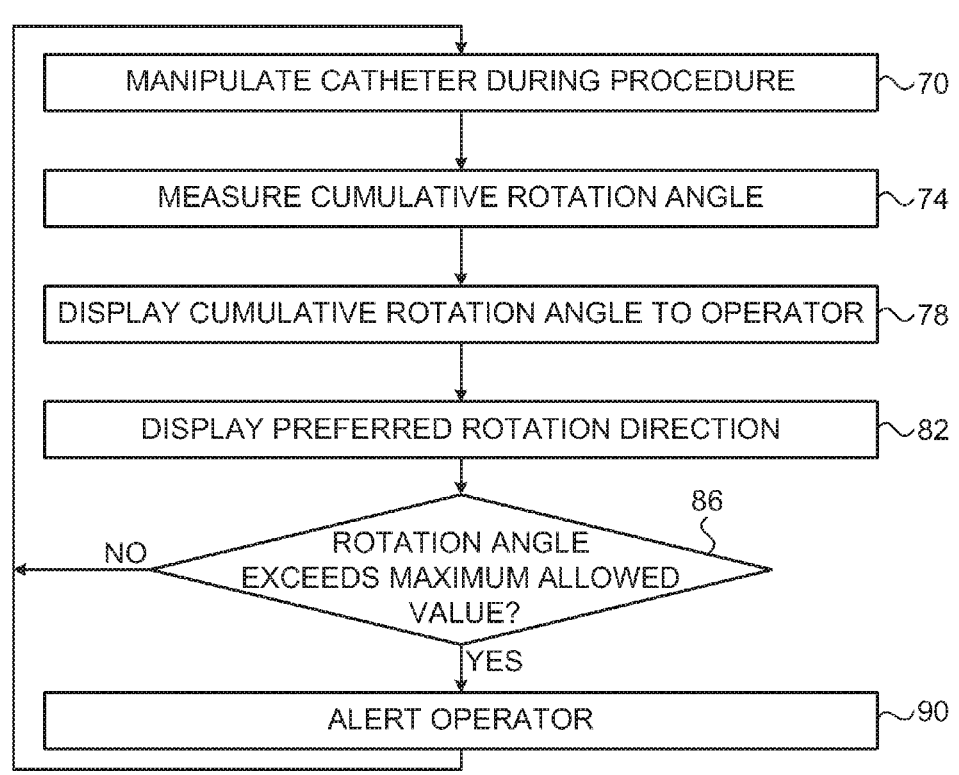
FIG. 3 is a flow chart that schematically illustrates a method for preventing catheter entanglement, in accordance with an embodiment of the present invention.

FIG. 3 is a flow chart that schematically illustrates a method for preventing catheter entanglement, in accordance with an embodiment of the present invention. The method begins with physician 24 maneuvering catheter 28 in the body of patient 30 as part of a medical procedure, at a catheter manipulation step 70. In particular, the physician applies rotation to the catheter.

Processor 48 measures the cumulative rotation angle applied to the catheter during the procedure, at an angle measurement step 74. Any suitable measurement method and sensor, such as the schemes described above, can be used. Processor 48 presents the measured cumulative rotation angle to the physician, at an angle presentation step 78. In some embodiments, processor 48 indicates the recommended direction for future rotations, at a direction recommendation step 82.

Processor 48 checks whether the current cumulative rotation angle exceeds the predefined maximum threshold, at a threshold checking step 86. If the current cumulative rotation angle is tolerable, the method loops back to step 70 above. Otherwise, processor 48 alerts the physician to the fact that the cumulative rotation angle is too high, at an alerting step 90.

Although the embodiments described herein mainly address catheter entanglement, the methods and systems described herein can also be used for avoiding entanglement in any other device (typically a hand-held device) that is connected by wire to a fixed point and is rotated by a user. Applications of these methods and systems may comprise medical applications (e.g., operating room applications), industrial applications or any other suitable applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus, comprising:
an elongated probe having proximal and distal ends;
a sensor coupled to the elongated probe and configured to generate signals used for determining location and orientation coordinates of the elongated probe;
a processor operatively connected to the sensor, the processor being configured to receive signals from the sensor indicative of the location and orientation coordinates of the elongated probe and subsequently determine a cumulative angle of rotation that is applied by an operator to the proximal end of the probe while the operator manipulates the proximal end so as to move the distal end within a body of a patient based on the signals; and
an output device operatively connected to the processor, the output device being configured to present an indication of the cumulative angle of rotation to the operator.

2. The apparatus according to claim 1, wherein the processor is configured to calculate the cumulative angle of rotation based on the location and orientation coordinates.

3. The apparatus according to claim 2, wherein the sensor comprises a magnetic position sensor that senses one or more externally-applied magnetic fields and produces the signals responsively to the sensed fields.

4. The apparatus according to claim 2, wherein the sensor is coupled to the proximal end of the probe.

5. The apparatus according to claim 2, wherein the sensor is coupled to the distal end of the probe.

6. The apparatus according to claim 1, wherein the output device is configured to alert the operator when the cumulative angle of rotation exceeds a predefined threshold.

7. The apparatus according to claim 1, wherein the output device is configured to indicate to the operator a preferred rotation direction that would reduce the cumulative angle of rotation.

8. The apparatus according to claim 1, wherein the output device is configured to display the cumulative angle of rotation alphanumerically to the operator.

9. Apparatus, comprising:
an elongated probe having proximal and distal ends and a longitudinal axis;
a sensor coupled to the elongated probe and configured to generate signals used for determining angular acceleration with respect to the longitudinal axis of the elongated probe;
a processor operatively connected to the sensor, the processor being configured to receive signals from the sensor indicative of the angular acceleration with respect to the longitudinal axis of the elongated probe and subsequently determine a cumulative angle of rotation that is applied by an operator to the proximal end of the probe while the operator manipulates the proximal end so as to move the distal end within a body of a patient based on the signals; and
an output device operatively connected to the processor, the output device being configured to present an indication of the cumulative angle of rotation to the operator.

* * * * *